United States Patent
Joudrey et al.

(10) Patent No.: US 9,492,764 B2
(45) Date of Patent: Nov. 15, 2016

(54) SYSTEM AND METHOD OF COOLING A PUMP HEAD USED IN CHROMATOGRAPHY

(75) Inventors: Kurt D. Joudrey, Chelmsford, MA (US); Paul E. Linderson, Warwick, RI (US)

(73) Assignee: Waters Technologies Corporation, Milford, MA (US)

( * ) Notice: Subject to any disclaimer, the term of this patent is extended or adjusted under 35 U.S.C. 154(b) by 354 days.

(21) Appl. No.: 14/002,035

(22) PCT Filed: Mar. 8, 2012

(86) PCT No.: PCT/US2012/028246
§ 371 (c)(1),
(2), (4) Date: Aug. 28, 2013

(87) PCT Pub. No.: WO2012/122361
PCT Pub. Date: Sep. 13, 2012

(65) Prior Publication Data
US 2013/0334117 A1    Dec. 19, 2013

Related U.S. Application Data

(60) Provisional application No. 61/451,209, filed on Mar. 10, 2011.

(51) Int. Cl.
*B01D 15/40* (2006.01)
*F04B 53/08* (2006.01)
(Continued)

(52) U.S. Cl.
CPC .............. *B01D 15/40* (2013.01); *F04B 53/08* (2013.01); *F04B 53/16* (2013.01); *F28D 1/00* (2013.01); *G01N 30/32* (2013.01)

(58) Field of Classification Search
CPC ............. F04B 15/08; F04B 9/02; F04B 9/025; F04B 53/08; F04B 53/16; F04B
(Continued)

(56) References Cited

U.S. PATENT DOCUMENTS 3,744,935 A * 7/1973 Magni ................. F04D 29/5886
417/366
4,597,720 A * 7/1986 Friedrichs ............... A47L 11/38
417/368
(Continued)

FOREIGN PATENT DOCUMENTS

DE    29507687 U1 * 8/1995    .............. F04B 17/03
EP    0672831 A2    9/1995
(Continued)

OTHER PUBLICATIONS

English language machine translation of DE 29507687 U1.*
(Continued)

*Primary Examiner* — David C Mellon
(74) *Attorney, Agent, or Firm* — Schmeiser, Olsen & Watts LLP

(57) ABSTRACT

An actuator has a support plate, a pump head in thermally conductive contact with the support plate, and an actuator body. Cooling means is disposed between the support plate and the actuator body. The cooling means is configured to remove and transfer heat from the pump head to the actuator body. In one embodiment, the cooling means includes two thermally conductive plates (called cold-side and hot-side plates) and a thermoelectric device disposed in thermally conductive contact between the cold-side and hot-side plates. The cold-side plate is in thermal communication with the pump head through the support plate. The hot-side plate is in thermal communication with the actuator body. The thermoelectric device is configured to transfer heat from the cold-side plate, which is in thermal communication with the pump head, to the hot-side plate, which is in thermal communication with the actuator body, thereby removing heat from the pump head.

8 Claims, 8 Drawing Sheets

(51) Int. Cl.
*F04B 53/16* (2006.01)
*G01N 30/32* (2006.01)
*F28D 1/00* (2006.01)

(58) Field of Classification Search
CPC ............ 2015/0818;F04B 39/06; F04B 39/064; F04B 2205/10; F04B 2205/11; F04B 2201/0801; F28D 1/00; B01D 15/40; F25B 21/02; F15B 21/042; F04D 29/5826; F04D 29/5866; G01N 30/32
See application file for complete search history.

(56) References Cited

U.S. PATENT DOCUMENTS

| | | | |
|---|---|---|---|
| 4,813,987 A | | 3/1989 | Chung et al. |
| 4,990,250 A | | 2/1991 | Hellinger |
| 5,087,360 A | * | 2/1992 | Wright ............... B01D 11/0203 210/181 |
| 5,180,293 A | | 1/1993 | Hartl et al. |
| 5,393,420 A | | 2/1995 | Hutchins et al. |
| 5,393,434 A | | 2/1995 | Hutchins et al. |
| 5,625,152 A | | 4/1997 | Pandorf et al. |
| 5,738,498 A | | 4/1998 | Allington et al. |
| 6,294,088 B1 | | 9/2001 | Allington et al. |
| 2002/0083733 A1 | | 7/2002 | Zhang et al. |
| 2003/0215341 A1 | | 11/2003 | Maiefski et al. |
| 2005/0115242 A1 | | 6/2005 | Conrad |
| 2006/0140778 A1 | | 6/2006 | Warren |
| 2010/0241076 A1 | | 9/2010 | Rush et al. |
| 2014/0190183 A1 | * | 7/2014 | Berger .................. F04B 39/064 62/3.2 |

FOREIGN PATENT DOCUMENTS

| | | |
|---|---|---|
| EP | 0990800 A1 | 4/2000 |
| EP | 1775478 A2 | 4/2007 |
| EP | 1803921 A2 | 7/2007 |
| JP | S62183080 U | 11/1987 |
| JP | S63215884 A | 9/1988 |
| JP | H0271148 A | 3/1990 |
| JP | H02248857 A | 10/1990 |
| JP | H0617756 A | 1/1994 |
| JP | H06234079 A | 8/1994 |
| JP | H1054688 A | 2/1998 |
| JP | 2000130355 A | 5/2000 |
| JP | 2005518529 A | 6/2005 |
| WO | 2010008851 A1 | 1/2010 |
| WO | WO 2011/149456 A1 * 12/2011 ............ F04B 39/064 |

OTHER PUBLICATIONS

International Search Report and Written Opinion in international patent application No. PCT/US12/28246, mailed on Jun. 20, 2012; 17 pages.
Partial Supplementary Search Report in counterpart European Patent Application No. 12755345.1, mailed on Jul. 30, 2015; 6 pages.
Notice of Rejection in related Japanese Patent Application No. 2013-557857, mailed on Jan. 5, 2016; 11 pages.
Extended Search Report in counterpart European Patent Application No. 12755345.1, mailed on Nov. 5, 2016; 11 pages.

* cited by examiner

SYSTEM AND METHOD OF COOLING A PUMP HEAD USED IN CHROMATOGRAPHY

CROSS REFERENCE TO RELATED APPLICATIONS

This application claims priority to U.S. Provisional Application No. 61/451,209, filed Mar. 10, 2011. The entire contents of U.S. Provisional Application No. 61/451,209 are incorporated herein by reference.

FIELD OF THE INVENTION

The invention relates generally to actuators. More specifically, the invention relates to systems and methods for cooling a pump head of an actuator.

INTRODUCTION

Supercritical fluid chromatography (SFC) uses highly compressible mobile phases, which typically employ carbon dioxide ($CO_2$) as a principle component. To ensure that the component remains liquid, the pump is chilled to a temperature below its critical temperature.

SUMMARY

In one aspect, the invention features an actuator with a support plate and a pump head secured to one side of the support plate. The pump head is in thermal contact with the support plate. An actuator body is secured to an opposite side of the support plate. Means for cooling is disposed between and in thermal communication with the support plate and the actuator body. The cooling means is configured to remove and transfer heat from the pump head to the actuator body.

In another aspect, the invention features an actuator having a thermally conductive member with an exterior surface, a pump head having a chamber for channeling pressurized fluid, and means for cooling the pump head. The cooling means is in thermal communication with the pump head internally. The cooling means is configured to remove and transfer heat from the pump head to the thermally conductive member with the exterior surface.

In still another aspect, the invention features a method for cooling a pump head of an actuator. The method comprises establishing thermally conductive contact between the pump head and a thermally conductive support plate, establishing thermally conductive contact between cooling means and the support plate, establishing thermally conductive contact between the cooling means and an actuator body, and electrically controlling the cooling means to remove and transfer heat from the pump head to the actuator body.

In still yet another aspect, the invention features a method for cooling a pump head of an actuator. The method comprises establishing thermal communication between the pump head and cooling means internally within the actuator, establishing thermal communication between the cooling means and a thermally conductive member of the actuator having an exterior surface, and electrically controlling the cooling means to remove and transfer heat from the pump head to the thermally conductive member with the exterior surface.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Cooling modules, described herein, for independently controlling the temperature of a pump head are installed internally within an actuator. In brief overview, such cooling modules remove heat from the pump head and transfers the heat to a member, feature, or component of the actuator with an exterior surface, preferably to the thermally conductive actuator body itself. In one embodiment, the cooling module is comprised of a thermoelectric device sandwiched between two thermally conductive plates. One of the plates is in thermal communication with the pump head (e.g., through a support plate), the other of the plates is in thermal communication with the actuator feature.

Advantageously, the cooling module can be invisible to the user; that is, for some embodiments, there are no new components in the customer-accessible areas of the actuator, the cooling module being disposed behind the support plate. From a maintenance point of view, no new procedures are needed to change pump head seals, as installation of a cooling module within the actuator requires no changes to the pump head components. Among these advantages, the solid state components used to produce the cooling module require no maintenance. The cooling module also improves the thermal stability of the pump head, improves control of density regardless of ambient temperature, and can achieve an accurate mass flow provided the pressure of the fluid is known.

Figure 1:
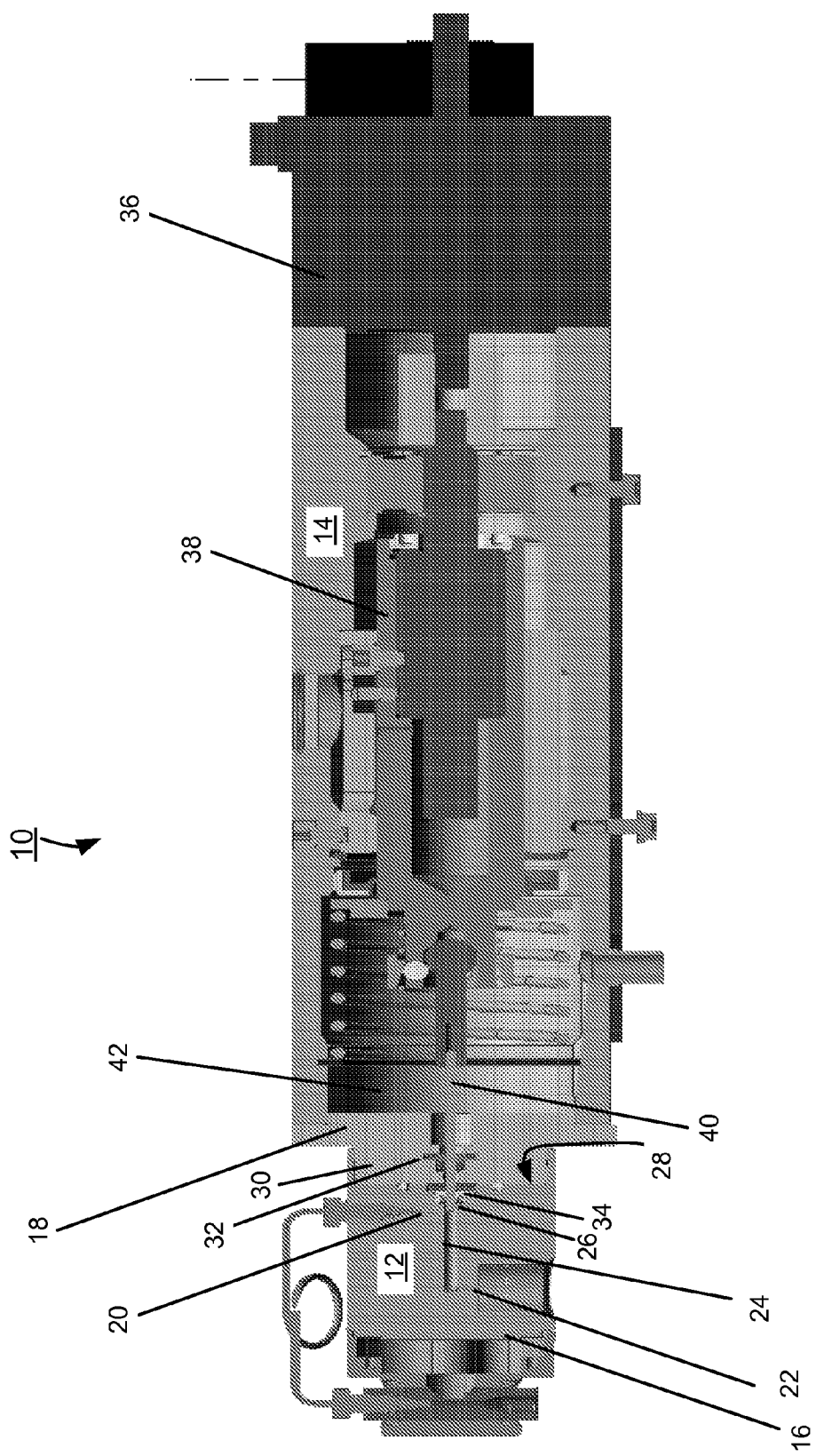
FIG. 1 is a cross-section diagrammatic view of an embodiment of an actuator that can configured with an internal cooling module for cooling a pump head.
Figure 2:
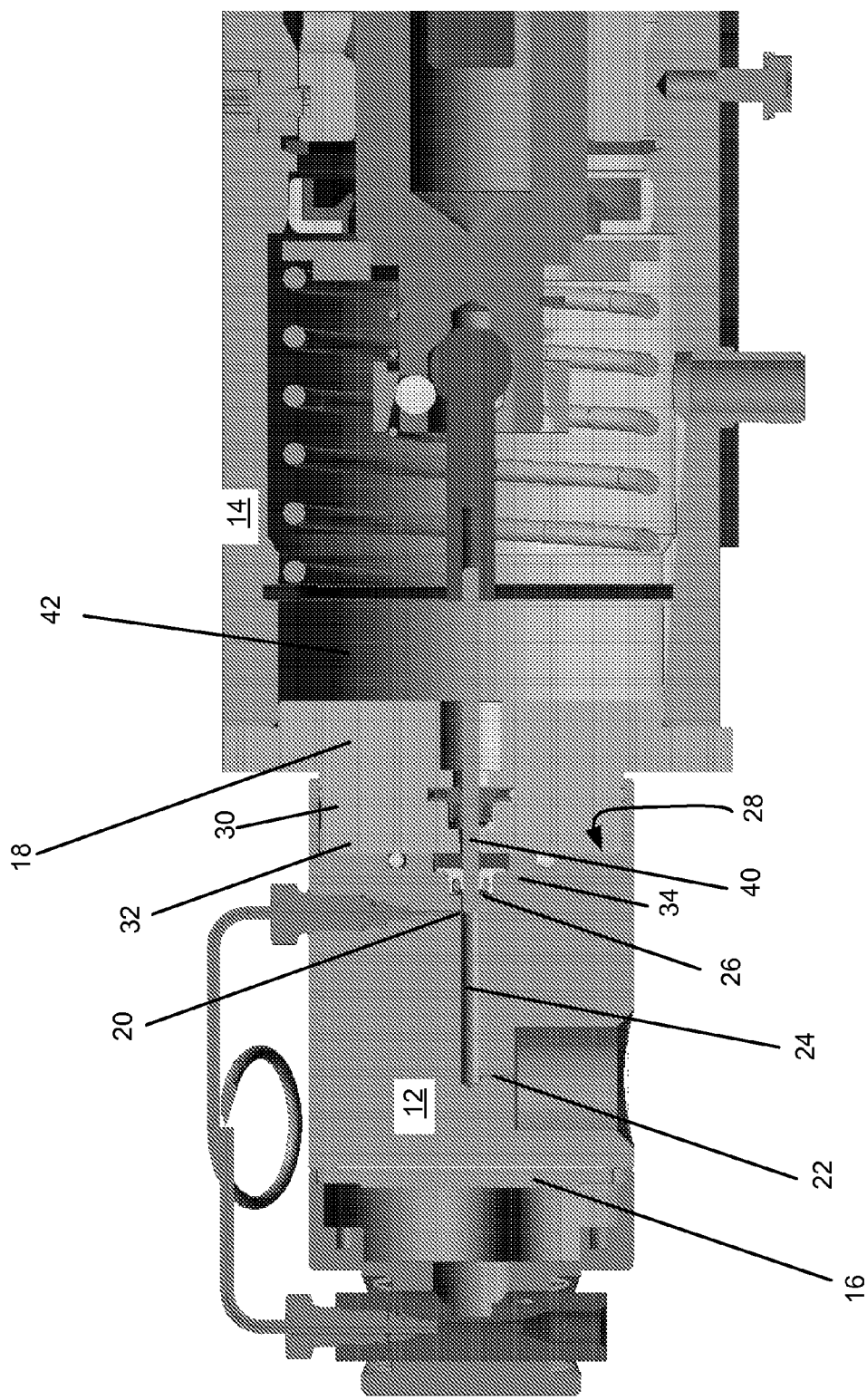
FIG. 2 is a closer view of the actuator.

FIG. 1 and FIG. 2 show an embodiment of an actuator 10 having a pump head 12 and an actuator body 14. (FIG. 2 is an enlarged view of the actuator 10 in the vicinity of the pump head 12.) The pump head 12 is secured at one end to a pressure transducer 16 and at its other end to one side of a support plate 18. Secured to the other side of the support plate 18 is the actuator body 14. In one embodiment, the actuator 10 is a part of a binary solvent manager (BSM), which uses two individual serial flow pumps to draw solvents from their reservoirs and deliver a solvent composition. An example implementation of a BSM is the ACQUITY® Binary Solvent Manager, manufactured by Waters Corp. of Milford, Mass.

The pump head 12 includes an outlet port 20, an inlet port 22, and a fluidic chamber 24, a bore opening 26, and a recess 28 for receiving and aligning a housing 30 that is also secured to the support plate 18. The fluidic chamber 24 within the pump head 12 is in fluidic communication with the outlet and inlet ports 20, 22 for receiving and discharging fluids, respectively. In some embodiments, the housing 30 provides a chamber within which to collect liquid and wash the plunger of any particulate that may form on the plunger surface. Seal assemblies, for example, low-pressure seal assembly 32 and high-pressure seal assembly 34, operate to contain the liquid in the housing 30.

The actuator body 14 includes a motor 36 and a drive mechanism 38 mechanically linked to a plunger 40. The plunger 40 extends through the bore opening 26 of the pump head 12 into the fluidic chamber 24. Although described in connection with reciprocating plungers, the cooling mechanisms described herein can also be used actuators with rotary shafts, such as a shaft that rotates and turns a rotor fitted to a stator. The term "rod" is used herein to broadly encompass plungers, shafts, rods, and pistons, whether reciprocating or rotary. Reference numeral 42 corresponds to a compartment in the actuator body 14 that can be adapted to accommodate a cooling module for controlling the temperature of the pump head 12, as illustrated in connection with FIG. 3.

Figure 3:
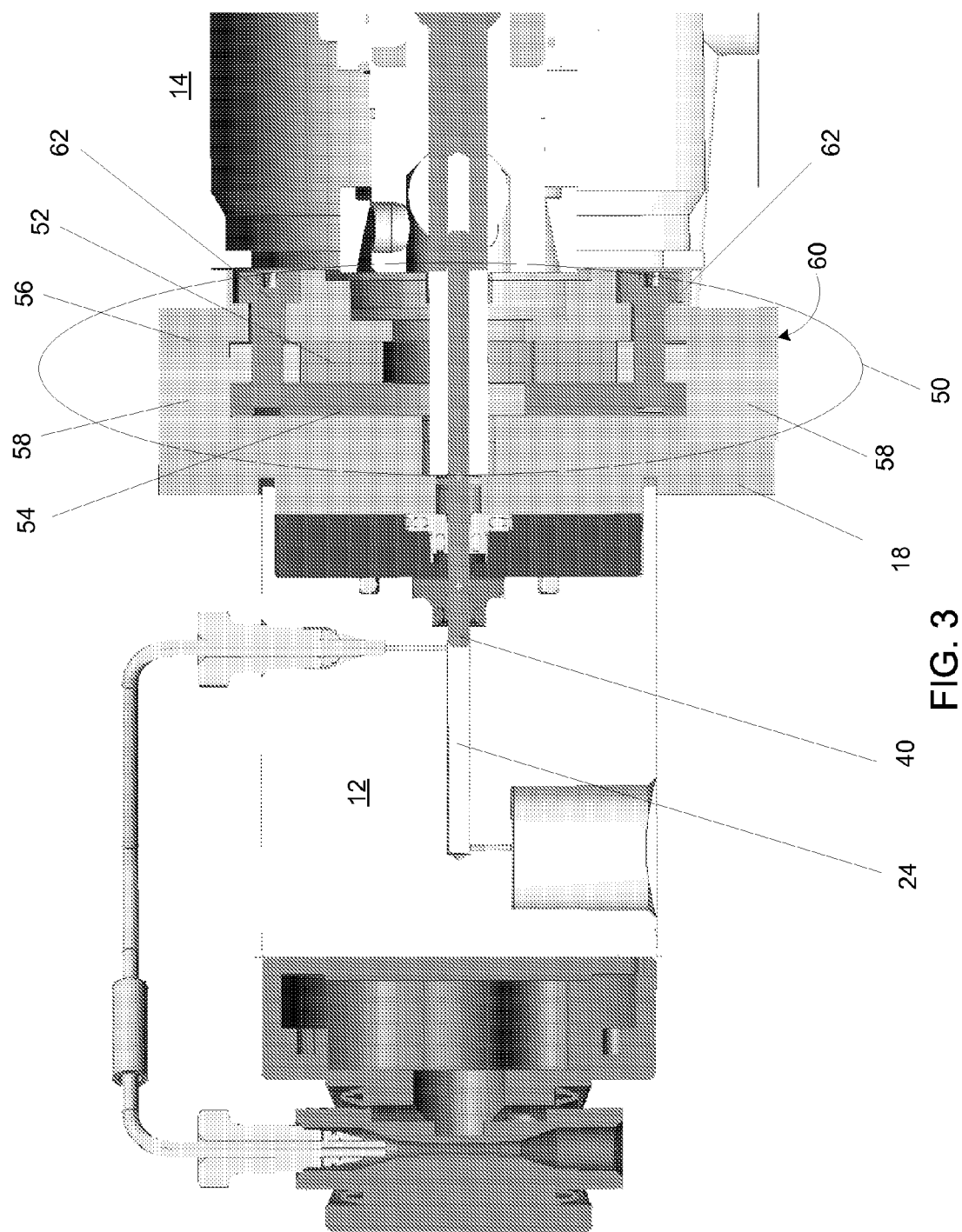
FIG. 3 is a cross-section of the actuator configured with one embodiment of an internal cooling module.

FIG. 3 is a cross-section of the actuator 10 configured with one embodiment of an internal cooling module 50 for providing independent control of cooling the pump head 12. The cooling module 50 includes a thermoelectric device 52 disposed between a cold-side plate 54 and a hot-side plate 56. In one embodiment, the thermoelectric device 52 is a Peltier device, which uses electrical power to produce a temperature difference between opposite sides of the device by operating as heat pumps that transfer heat from one side to the other. The temperature difference produced depends on several variables: material properties of the thermoelectric device 52, the amount of heat being removed from the cold side, the average temperature of the chambers, and the drive current/voltage. In this embodiment, the thermoelectric device has a center hole to accommodate the plunger 40. Thermoelectric devices of other geometries can be employed, provided they do not interfere with the movement of the plunger.

The cold-side plate 54 is in thermally conductive contact with the support plate 18. The material of the support plate 18 is selected to enhance thermal conductivity. The hot-side plate 56 is in thermally conductive contact with the actuator body 14. Other thermally conductive members, features, or components of the actuator, other than or in addition to the actuator body 14, can operate as a hot-side sink. The plates 54, 56 also have a central hole to accommodate the plunger 40. Electrodes (not shown) for controlling the operation of the thermoelectric chip 52 extend between the insulator 58 and hot-side plate 56. In one embodiment, the hot-side plate 56 is made of copper. An insulator 58 is disposed around the cold-side plate 54 and the thermoelectric chip 52, to insulate them from the ambient environment and to minimize the thermal communication between the hot and cold surfaces. The hot-side plate 56 has an exterior surface 60 so that heat can radiate directly from the hot side plate 56 into the ambient environment. Fasteners 62 secure the cooling module 50 to the support plate 18. During operation of the cooling module, the cold-side plate 54 draws heat from the pump head 12 and transfers the heat to the hot-side plate 56. From the hot-side plate 56, the heat transfers to the actuator body 14, from which heat radiates, conducts or convects into the ambient environment. A heat sink, fan, and/or liquid cooling of the hot side can be used to cool the hot side.

Temperature measurement for feedback control purposes can be made at one or more locations within the actuator. In preferred embodiments, a temperature sensor is disposed on or near the cold-side plate 54.

Figure 4A:
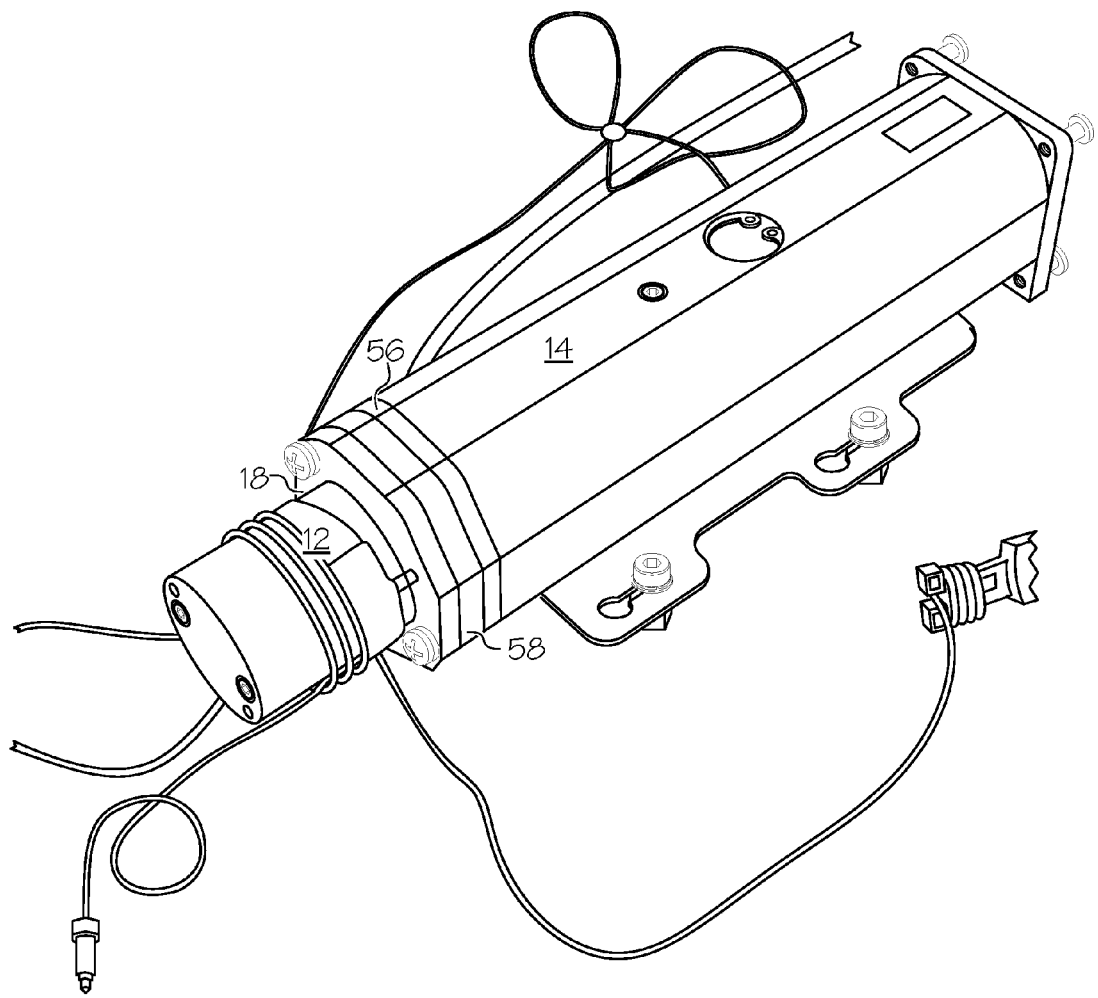
FIG. 4A and FIG. 4B show an actuator configured with an internal cooling module.
Figure 4B:
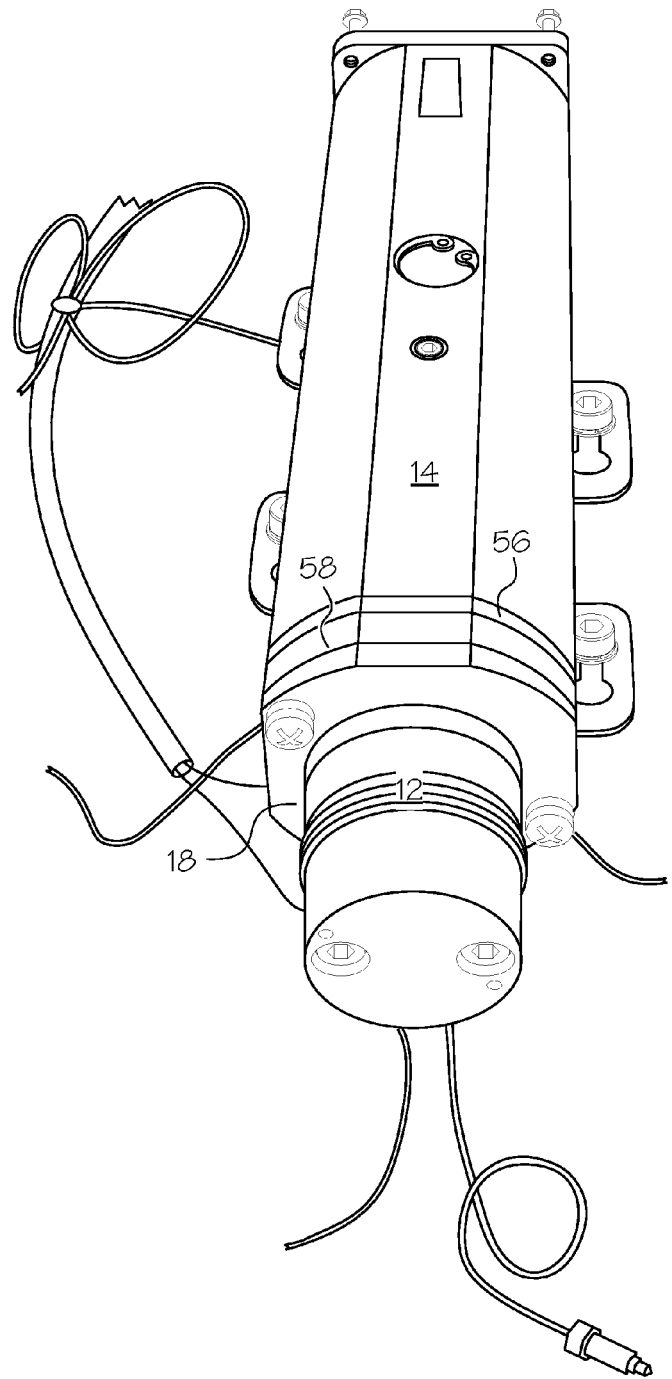

FIG. 4A and FIG. 4B show two different views of an actuator configured with an internal cooling module. Visible features of the cooling module are the hot-side plate 56 and the insulator 58.

Figure 5:
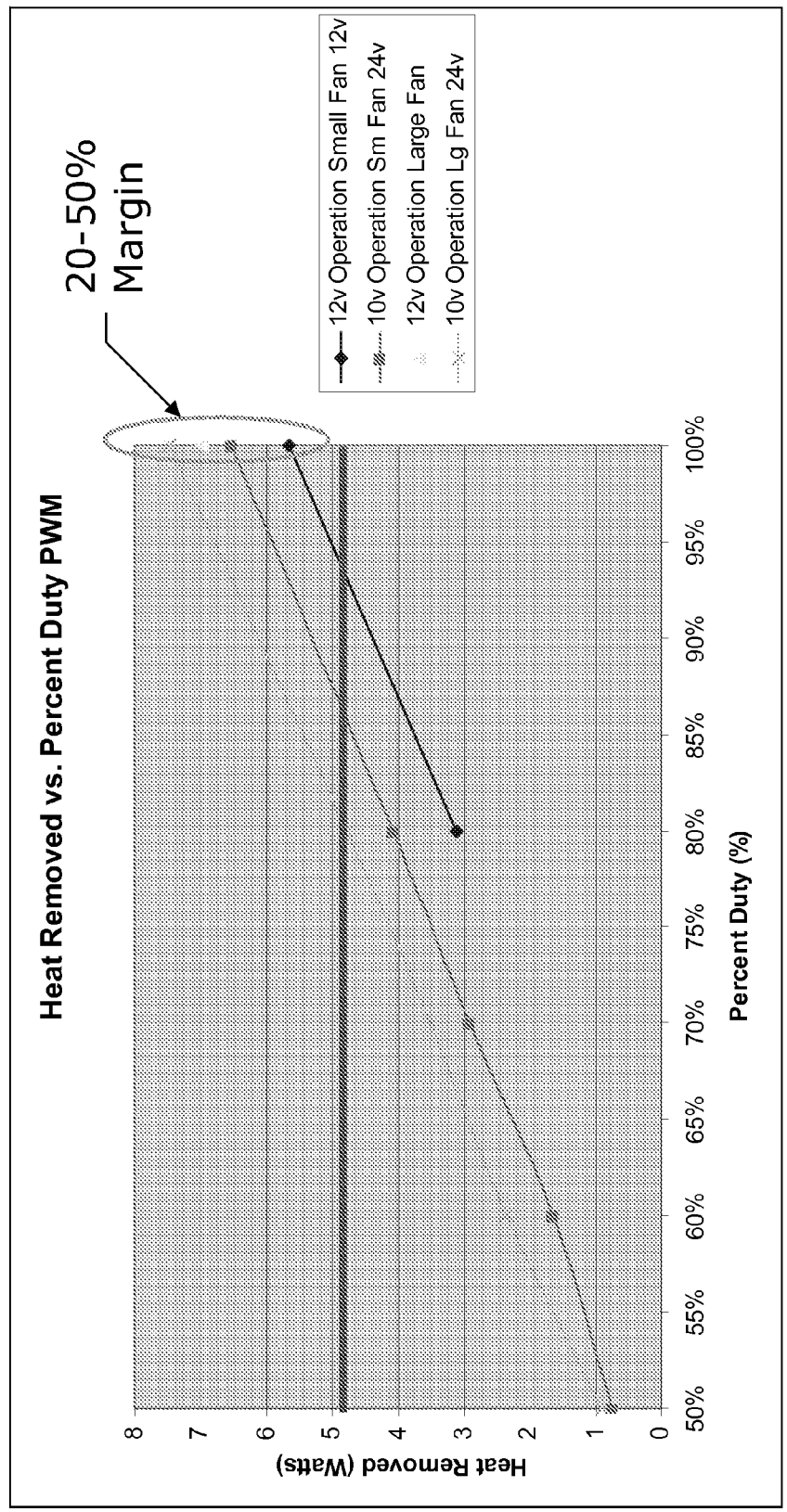
FIG. 5 is a graph of test results produced by the internal cooling module.

FIG. 5 is a graph of test results produced by one embodiment of internal cooling module. The x-axis corresponds to the duty cycle at which the Peltier device 52 is operated. On the y-axis is the amount of heat removed (in Watts) from the pump head, the heat being transferred from the cold side plate to the hot side plate. Four plots appear on the graph, each representing one of four tested combinations of operating voltage of the Peltier device, which was either 10 v or 12 v, and the fan size, which was either small or large. The horizontal red line represents the preferred amount of heat to be removed. The four plots show that when the cooling module is operated at 100% duty cycle, the amount of heat removed provides a 20-50% margin with respect to the preferred amount of heat to be removed.

Figure 6:
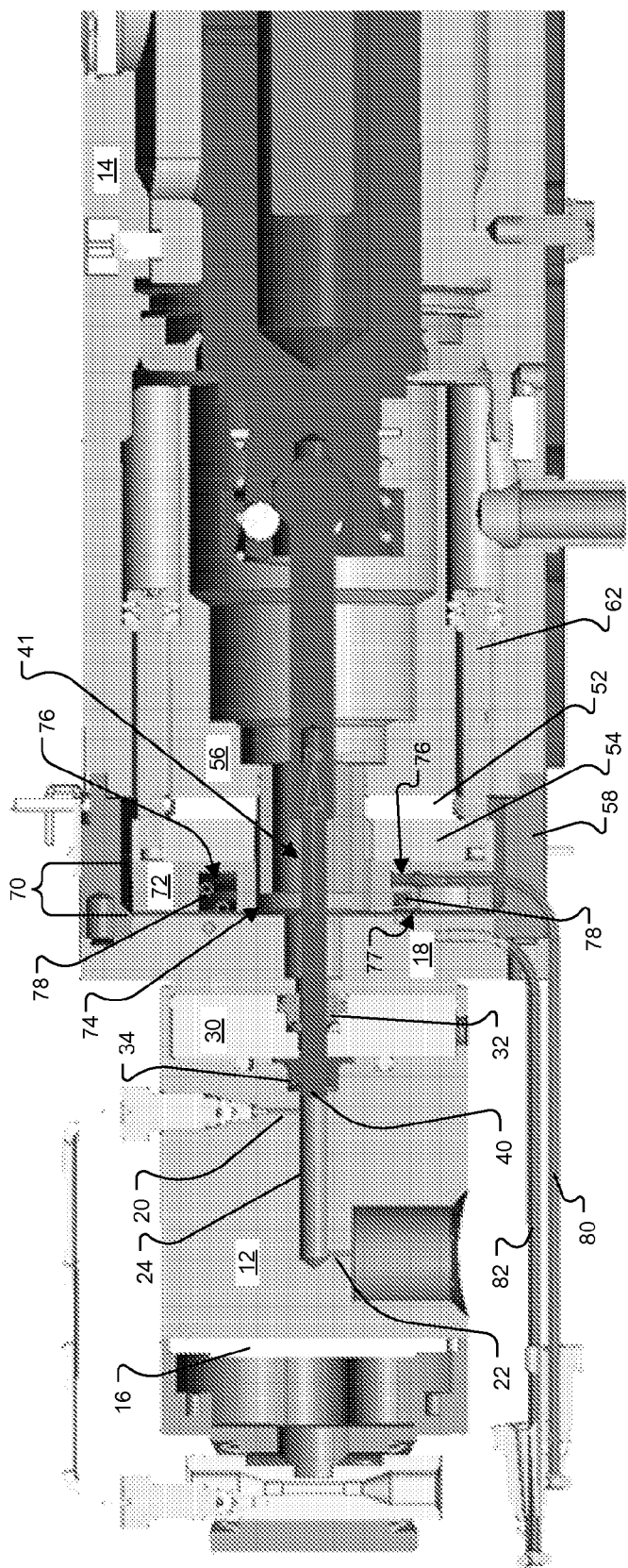
FIG. 6 is a cross-section of the actuator configured with one embodiment of a pre-chiller unit.

In another embodiment, a pre-chiller unit is disposed (e.g., bolted) between the support plate 18 and the cold-side plate 54 of the cooling module 50. FIG. 6 is a cross-section of the actuator 10 configured with such a pre-chiller unit 70. The pre-chiller unit 70 operates to chill the fluid before the fluid enters the fluidic chamber 24.

The pre-chiller unit 70 includes a pre-chiller body 72 that is in thermally conductive contact with the support plate 18 and the cold-side plate 54. The pre-chiller body 72 is formed of a thermally conductive material (e.g., copper). The pre-chiller body 72 defines a though hole 74 which accommodates the plunger 40.

Increasing the number of components, by adding the pre-chiller unit 70, between the actuator body 14 and the pump head 12 creates a worse tolerance stack up. To help overcome this, the length of the plunger 40 behind the low pressure seal assembly 32 (the proximal end portion 41 of the plunger 40) can be provided with an extended length.

The pre-chiller unit 70 also includes fluidic tubing 76 that is disposed within a recess 77 in the pre-chiller body 70 and is in thermal communication with the pre-chiller body 70. The fluidic tubing 76 is held in the recess 77 with thermal epoxy. Alternatively or additionally, thermal grease could be used in the recess 77 to establish thermal heat transfer between the pre-chiller body 70 and the fluidic tubing 76. Alternatively or additionally, solder could be used to hold the fluidic tubing 76 within the recess 77 and establish thermal communication with the pre-chiller body 70. Channels could be machined in the copper plate instead as well. The fluidic tubing 76 includes five (5) turns of 0.040 inner diameter stainless steel tube 78 which encircle the through hole 74 and define the fluid volume of the pre-chiller unit 70. The fluid volume of the pre-chiller unit 70 is preferably larger than the fluid volume of the fluidic chamber 24 (that is, the volume available to receive fluid when the plunger 40 is at the end of its intake stroke), e.g., greater than about 140 µL. In this regard, the pre-chiller unit 70 can have a fluid volume of about 400 µL and about 500 µL, e.g., about 426 µL. The fluid volume of the pre-chiller unit 70 can be about three times greater than the fluid volume of the fluidic chamber 24. The fluidic tubing 76 includes an inlet 80 and outlet 82 that are connected to or integral with the tube 78 and which allow for external fluidic connection to be made.

During operation, the cold-side plate 54 draws heat from the pre-chiller unit 70 and transfers it to the hot-side plate 56. From the hot-side plate 56, the heat transfers to the actuator body 14, from which heat radiates, conducts, or convects into the ambient environment. The cooling of the pre-chiller unit 70 also has the effect of cooling the pump head 12 via the thermally conductive contact between the pump head 12 and the support plate 18, and between the support plate 18 and the pre-chiller unit 70.

Figure 7:
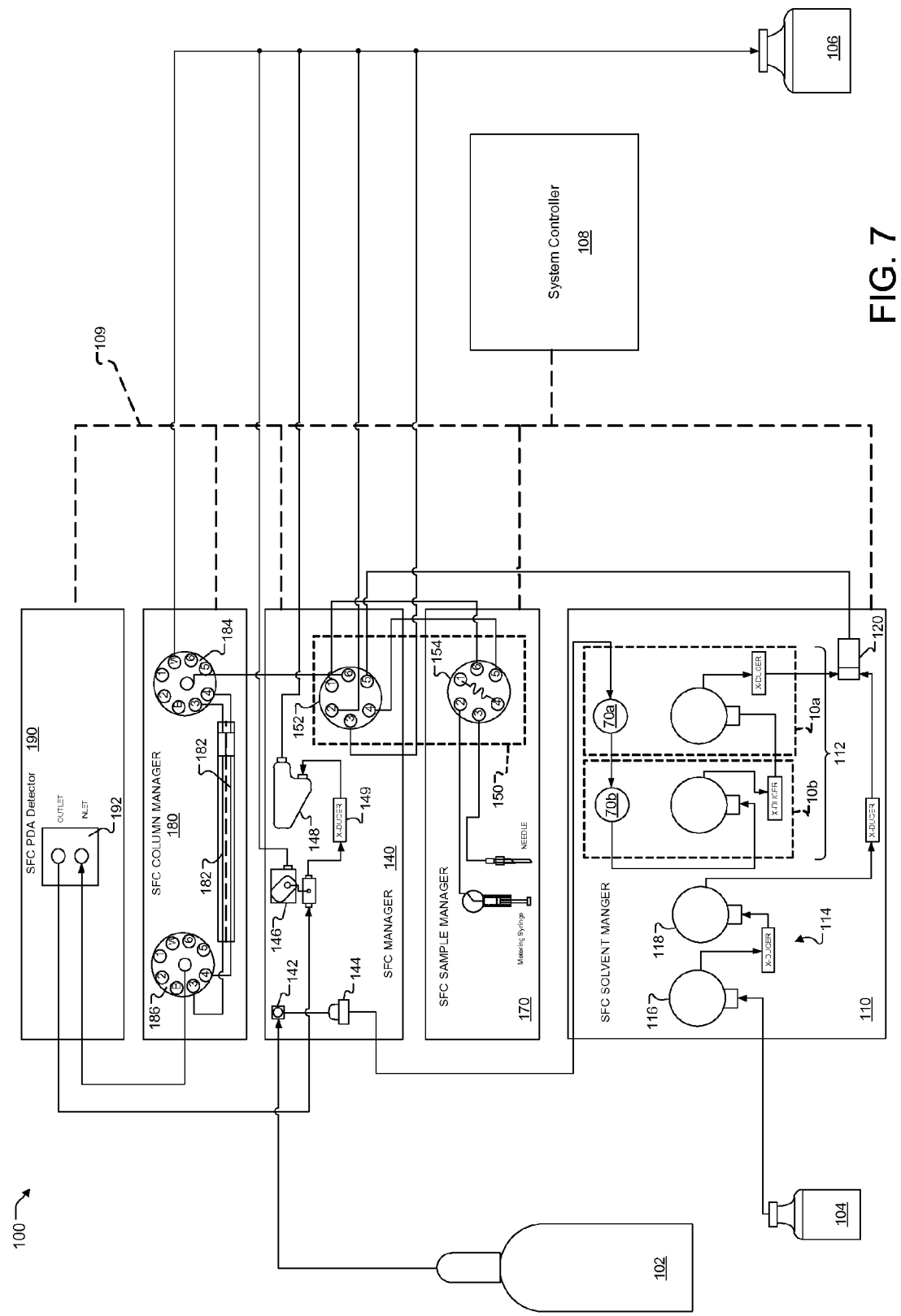
FIG. 7 is a supercritical fluid chromatography system that utilizes an actuator as illustrated in FIG. 6.

FIG. 7 illustrates a supercritical fluid chromatography system 100 which utilizes actuator 10 of FIG. 6. The SFC system 100 includes a plurality of stackable modules including a solvent manager 110; an SFC manager 140; a sample manager 170; a column manager 180; and a detector module 190.

The solvent manager 110 is comprised of a first pump 112 which receives carbon dioxide ($CO_2$) from $CO_2$ source 102 (e.g., a tank containing compressed $CO_2$). The $CO_2$ passes through an inlet shutoff valve 142 and a filter 144 in the SFC manager 140 on its way to the first pump 112. The first pump 112 comprises an accumulator actuator 10a and a primary actuator 10b connected in series. The accumulator actuator 10a delivers $CO_2$ to the system 100. The primary actuator 10b refills the accumulator actuator 10a and delivers $CO_2$ to the system 100 while refilling the accumulator actuator 10a.

The accumulator actuator 10a and the primary actuator 10b each have the construction illustrated in FIG. 6 and are arranged to perform a multistep pre-chilling of the $CO_2$. The $CO_2$ travels from the SFC manager 140 and through a pre-chiller unit 70a of the accumulator actuator 10a. The accumulator actuator 10a is controlled to a temperature of about 12° C. via its internal cooling module. After passing through the pre-chiller unit 70a of the accumulator actuator 10a, the $CO_2$ travels through a pre-chiller unit 70b of the primary actuator 10b. The primary actuator 10b is controlled to a temperature of about 2° C. via its internal cooling module.

After passing through both of the pre-chiller units 70a, 70b at relatively low pressure (e.g., about 700 psi to about 1200 psi) the $CO_2$ is passed through the fluidic chamber (see, e.g., item 24 in FIG. 6) of the primary actuator 10b and then through the fluidic chamber of the accumulator actuator 10a.

Since the accumulator actuator 10a is controlled to 12° C., the $CO_2$ might be in gas form when it passes through the pre-chiller unit 70a of the accumulator actuator 10a. To help ensure that the $CO_2$ is delivered to the system 100 in liquid form, the primary actuator 10b is relied on to condense the $CO_2$ to liquid. Having the fluid volume of the pre-chiller 70b greater than the volume of the primary actuator's fluidic chamber (i.e., when its plunger reaches the end of its intake stroke) can help ensure that a sufficient volume of $CO_2$ is available to enable the primary actuator 10b to condense it to liquid before it passes through the pump head of the accumulator actuator 10a.

The accumulator actuator 10a serves as a metering device which meters the flow of $CO_2$ into the system 100. The ability to control the temperature of the accumulator actuator 10a (e.g., via its internal cooling module) can be particularly beneficial. More specifically, mass flow is dependent on temperature as well as pressure and volume flow rate. Thus, the ability to control temperature can allow for more accurate mass flow, which, in turn, can provide for more accurate chromatography.

In some cases, the solvent manager 110 also includes a second pump 114, which can comprise a primary actuator 116 and an accumulator actuator 118 connected in series, for receiving an organic co-solvent (e.g., methanol, water ($H_2O$), etc.) from an organic co-solvent source 104. The accumulator actuator 118 delivers co-solvent to the system 100. The primary actuator 116 delivers co-solvent to the system 100 while refilling the accumulator actuator 118. Transducers are connected to outlet ports of the respective pump heads for monitoring pressure. The solvent manager 110 also includes electrical drives for driving the primary and accumulator actuators of the first and second pumps 112, 114. The $CO_2$ and organic co-solvent fluid flows are mixed at a tee 120 forming a mobile phase fluid flow that continues to an injection valve subsystem 150, which injects a sample plug for separation into the mobile phase fluid flow.

In the illustrated example, the injection valve subsystem 150 is comprised of an auxiliary valve 152 that is disposed in the SFC manager 140 and an inject valve 154 that is disposed in the sample manager 170. The auxiliary valve 152 and the inject valve 152 are fluidically connected and the operations of these two valves are coordinated to introduce a sample plug into the mobile phase fluid flow. The inject valve 154 is operable to draw up a sample plug from a sample source (e.g., a vial) in the sample manager 170 and the auxiliary valve 152 is operable to control the flow of mobile phase fluid into and out of the inject valve 154. The SFC manager 140 also includes a valve actuator for actuating the auxiliary valve 152 and electrical drives for driving the valve actuations. Similarly, the sample manager 170 includes a valve actuator for actuating the inject valve and 154 and electrical drives for driving the valve actuations.

From the injection valve subsystem 150, the mobile phase flow containing the injected sample plug continues through a separation column 182 in the column manager 180, where the sample plug is separated into its individual component parts. The column manager 180 comprises a plurality of such separation columns, and inlet and outlet switching valves 184, 186 for switching between the various separation columns.

After passing through the separation column 182, the mobile phase fluid flow continues on to a detector 192 (e.g., a flow cell/photodiode array type detector) housed within the detector module 190 then through a vent valve 146 and then on to a back pressure regulator 148 in the SFC manager 140 before being exhausted to waste 106. A transducer 149 is provided between the vent valve 146 and the back pressure regulator 148.

The back pressure regulator 148 is adjustable to control or modify the system fluid pressure. This can allow the pressure to be changed from run to run. The properties of $CO_2$ affect how quickly compounds are extracted from the separation column 182, so the ability to change the pressure can allow for different separation based on pressure. Generally, the back pressure regulator 148 can be used to maintain the system pressure in the range of about 1500 psi to about 6000 psi.

Also shown schematically in FIG. 7 is a computerized system controller 108 that can assist in coordinating operation of the SFC system 100. Each of the individual modules 110, 140, 170, 180, 190 also includes its own control electronics, which can interface with each other and with the system controller 108 via an Ethernet connection 109. The control electronics for each module can include non-volatile memory with computer-readable instructions (firmware) for controlling operation of the respective module's components (e.g., the pumps, valves, etc.) in response to signals received from the system controller 108 or from the other modules. Each module's control electronics can also include at least one processor for executing the computer-readable instructions, receiving input, and sending output. The control electronics can also include one or more digital-to-analog (D/A) converters for converting digital output from one of the processors to an analog signal for actuating an associated one of the pumps or valves (e.g., via an associated pump or valve actuator). The control electronics can also include one or more analog-to-digital (A/D) converters for converting an analog signal, such as from system sensors (e.g., pressure transducers), to a digital signal for input to one of the processors. In some cases, some or all of the various features of these control electronics can be integrated in a microcontroller.

While an embodiment has been described in which a pre-chiller is utilized to chill fluid before the fluid enters the fluidic chamber of a pump head, another embodiment can use a pre-chiller unit to chill the fluid after the fluid leaves the pump head.

While the invention has been shown and described with reference to specific preferred embodiments, it should be understood by those skilled in the art that various changes in form and detail may be made therein without departing from the spirit and scope of the invention as defined by the following claims. For example, although described herein primarily with respect to reciprocating plunger applications, the various embodiments of cooling systems can also be used in rotary applications. Moreover, other heat removal means can be used in conjunction with the cooling module described herein in order to remove larger loads, if necessary. In addition, although described with respect to SFC applications, the principles can be implemented in actuators used in any other type of application for which temperature control of the pump head is desired. For instance, temperature control of the pump head may produce more repeatable and accurate results for other types of liquid chromatography applications, such as HPLC and UPLC, regardless of the ambient temperature.

What is claimed is:

1. An actuator comprising:

A support plate;

A pump head comprising an outlet port, an inlet port, a fluidic chamber extending between the outlet and inlet ports, and a bore opening, the pump head being secured to one side of the support plate and being in thermal contact with the support plate;

An actuator body secured to an opposite side of the support plate from the pump head;

A plunger which extends through the bore opening of the pump head into the fluidic chamber, the plunger being displaceable between a first, delivery end of stroke position and a second, intake end of stroke position; and A pre-chiller unit disposed between the support plate and the actuator body and comprising a pre-chiller body and a fluidic tubing in thermal communication with the pre-chiller body, the pre-chiller unit being in thermal communication with the support plate for cooling a fluid flow before the fluid flow enters the pump head, wherein a fluid volume of the fluidic tubing is greater than a fluidic volume of the fluidic chamber when the plunger is in the intake end of stroke position.

2. The actuator of claim 1, wherein the fluid volume of the fluidic tubing is at least two times greater than the fluidic volume of the fluidic chamber when the plunger is in the intake end of stroke position.

3. The actuator of claim 1, wherein the fluid volume of the fluidic tubing is at least three times greater than a fluidic volume of the fluidic chamber when the plunger is in the intake end of stroke position.

4. The actuator of claim 1, wherein the pre-chiller body defines a recess, and wherein the fluidic tubing is disposed within the recess.

5. The actuator of claim 1, wherein the pre-chiller body is made of copper and the fluidic tubing is made of stainless steel.

6. The actuator of claim 1, further comprising a cooling module arranged to cool the pre-chiller unit, wherein the pre-chiller unit is disposed between and in thermal communication with the support plate and the cooling module.

7. The actuator of claim 6, wherein the cooling module comprises:

a pair of thermally conductive plates, one of the thermally conductive plates being in thermal communication with the pre-chiller unit, the other of the thermally conductive plates being in thermal communication with the actuator body; and a thermoelectric device between and in thermally conductive contact with the pair of thermally conductive plates, the thermoelectric device being configured to transfer heat from the thermally conductive plate that is in thermal communication with the pre-chiller unit to the other thermally conductive plate that is thermal communication with the actuator body.

8. The actuator of claim 6, wherein the cooling module is configured to cool the pump head via thermally conductive communication between the cooling module, the pre-chiller unit, the support plate, and the pump head.

* * * * *